(12) United States Patent
Zakelj

(10) Patent No.: US 11,116,645 B2
(45) Date of Patent: Sep. 14, 2021

(54) ALIF SPINE IMPLANT WITH CAM SCREWS FOR INHIBITING BONE ANCHOR BACKOUT

(71) Applicant: Life Spine, Inc., Huntley, IL (US)

(72) Inventor: Paul C. Zakelj, Chicago, IL (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 16/863,361

(22) Filed: Apr. 30, 2020

(65) Prior Publication Data

US 2020/0345512 A1 Nov. 5, 2020

Related U.S. Application Data

(60) Provisional application No. 62/840,475, filed on Apr. 30, 2019.

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/3081* (2013.01); *A61F 2002/30784* (2013.01); *A61F 2002/30841* (2013.01); *A61F 2002/30985* (2013.01); *A61F 2310/00023* (2013.01)

(58) Field of Classification Search
CPC .......... A61F 2/44; A61F 2/4455; A61F 2/446; A61F 2/4465; A61F 2/447; A61F 2002/30517; A61F 2002/30578; A61F 2002/30784; A61F 2002/30787; A61F 2002/3081; A61F 2310/00023

See application file for complete search history.

(56) References Cited

U.S. PATENT DOCUMENTS

| | | | |
|---|---|---|---|
| 9,675,465 B2 * | 6/2017 | Padovani | A61F 2/442 |
| 10,137,002 B2 * | 11/2018 | Padovani | A61F 2/442 |
| 10,524,929 B2 * | 1/2020 | Shoshtaev | A61F 2/4455 |
| 10,751,185 B2 * | 8/2020 | Dawson | A61L 27/225 |
| 2010/0057206 A1 * | 3/2010 | Duffield | A61F 2/30771 623/17.16 |
| 2012/0303128 A1 * | 11/2012 | Ullrich, Jr. | A61F 2/442 623/17.16 |
| 2014/0039623 A1 * | 2/2014 | Iott | A61F 2/442 623/17.16 |
| 2014/0277461 A1 * | 9/2014 | Nebosky | A61F 2/442 623/17.11 |

(Continued)

*Primary Examiner* — Eric S Gibson
(74) *Attorney, Agent, or Firm* — Foley & Lardner LLP

(57) ABSTRACT

A spine implant for an ALIF procedure includes anchoring members being either a bone screw or flexible barb, each having a head on one end of a shaft, and a tip on another end of the shaft. The spine implant includes a porous cage having a front, rear, central cavity, and three angled bores in the front that extend into the central cavity configured to receive one of the plurality of anchoring members such that the tip of the anchoring member extends from one or another side of the cavity with its head retained in the front. The spine implant further includes two retention members configured for insertion into the front such that a portion of the two retention members are positioned over the heads of two, adjacent anchoring members to inhibit bone anchor backout via cam action between the retention member and the heads of the anchoring members.

10 Claims, 12 Drawing Sheets

(56) References Cited

U.S. PATENT DOCUMENTS

| | | | |
|---|---|---|---|
| 2015/0328005 A1* | 11/2015 | Padovani | A61F 2/30744 623/17.13 |
| 2016/0022431 A1* | 1/2016 | Wickham | A61F 2/447 623/17.16 |
| 2016/0038301 A1* | 2/2016 | Wickham | A61F 2/4455 623/17.16 |
| 2016/0270920 A1* | 9/2016 | Dawson | A61F 2/4601 |
| 2016/0310295 A1* | 10/2016 | Reed | A61F 2/4611 |
| 2016/0374829 A1* | 12/2016 | Vogt | A61F 2/4465 623/17.16 |
| 2017/0020685 A1* | 1/2017 | Geisler | A61F 2/442 |
| 2017/0182222 A1* | 6/2017 | Paddock | A61F 2/447 |
| 2017/0245998 A1* | 8/2017 | Padovani | A61F 2/442 |
| 2018/0104063 A1* | 4/2018 | Asaad | A61F 2/447 |
| 2018/0110624 A1* | 4/2018 | Arnone | A61F 2/30767 |
| 2018/0110627 A1* | 4/2018 | Sack | A61F 2/4465 |
| 2018/0296363 A1* | 10/2018 | Berry | A61F 2/3094 |
| 2018/0303623 A1* | 10/2018 | Shoshtaev | A61F 2/4455 |
| 2018/0303624 A1* | 10/2018 | Shoshtaev | A61F 2/4611 |
| 2018/0318099 A1* | 11/2018 | Altarac | A61F 2/4455 |
| 2019/0000636 A1* | 1/2019 | Kim | A61F 2/4455 |
| 2019/0046329 A1* | 2/2019 | Padovani | A61F 2/44 |
| 2019/0076258 A1* | 3/2019 | Black | B33Y 80/00 |
| 2019/0091027 A1* | 3/2019 | Asaad | A61F 2/447 |
| 2019/0201212 A1* | 7/2019 | Gilbride | A61F 2/28 |
| 2019/0254840 A1* | 8/2019 | Gray | A61F 2/4455 |
| 2019/0298542 A1* | 10/2019 | Kloss | A61F 2/30767 |
| 2019/0328546 A1* | 10/2019 | Palagi | A61F 2/447 |
| 2019/0343652 A1* | 11/2019 | Petersheim | A61F 2/4455 |
| 2020/0000595 A1* | 1/2020 | Jones | B33Y 80/00 |
| 2020/0060831 A1* | 2/2020 | Rathbun | A61F 2/30771 |
| 2020/0078191 A1* | 3/2020 | Ehteshami | A61F 2/447 |
| 2020/0100906 A1* | 4/2020 | Ball | A61F 2/442 |
| 2020/0138595 A1* | 5/2020 | Shoshtaev | A61F 2/4611 |
| 2020/0179128 A1* | 6/2020 | Stalcup | A61F 2/442 |
| 2020/0222191 A1* | 7/2020 | Arnone | A61F 2/447 |
| 2020/0222203 A1* | 7/2020 | Shoshtaev | A61F 2/4611 |
| 2020/0289288 A1* | 9/2020 | Muller | B33Y 80/00 |
| 2020/0297505 A1* | 9/2020 | McLaughlin | A61F 2/28 |
| 2020/0323645 A1* | 10/2020 | Northcutt | A61F 2/30942 |
| 2020/0345512 A1* | 11/2020 | Zakelj | A61F 2/447 |
| 2020/0375758 A1* | 12/2020 | Northcutt | A61F 2/28 |
| 2021/0038403 A1* | 2/2021 | Neary | A61F 2/30771 |
| 2021/0059834 A1* | 3/2021 | Miguel | A61F 2/30749 |
| 2021/0077267 A1* | 3/2021 | Morrison | A61F 2/447 |

* cited by examiner

ALIF SPINE IMPLANT WITH CAM SCREWS FOR INHIBITING BONE ANCHOR BACKOUT

CROSS-REFERENCE TO RELATED APPLICATIONS

This U.S. non-provisional patent application claims the benefit of and/or priority under 35 U.S.C. § 119(e) to U.S. provisional patent application Ser. No. 62/840,475 filed Apr. 30, 2019 titled "ALIF Spine Implant With Cam Screws for Inhibiting Bone Anchor Backout" the entire contents of which is specifically incorporated herein by reference.

FIELD OF THE INVENTION

The present invention relates to methods and devices for orthopedic surgery of the spine and, particularly, to methods and devices for anterior lumbar interbody fusion (ALIF).

BACKGROUND OF THE INVENTION

Many people contend with spine issues as a result of age, disease, and trauma, as well as congenital and acquired complications and conditions. Some of the issues can only be corrected with spinal surgery. While some of these issues can be alleviated without surgery, other issues necessitate surgery. Many people contend with spine issues as a result of age, disease, and trauma, as well as congenital and acquired complications and conditions. Spinal fusion may be recommended for conditions such as spondylolistheses, degenerative disc disease, or recurrent disc herniation, and is designed to create solid bone between adjacent vertebrae, thereby eliminating any movement between the vertebrae. A spinal fusion uses an implant or device known as an interbody cage or spacer along with a bone graft and/or a bone graft substitute that is inserted into the disc space between adjacent vertebrae from one side of the spine. Typically additional surgical hardware (implants) such as pedicle screws, rods, or plates are attached to the back if the vertebrae. As the bone graft heals, it fuses the adjacent vertebrae to form one long vertebra.

A fusion of the lumbar region of the spine (a lumbar fusion) may be accomplished using several techniques. One such technique is known as anterior lumbar interbody fusion or ALIF. ALIF spine surgery is performed through the anterior aspect of the spine and provides stabilization of the spine. In an ALIF, the disc space is fused by approaching the spine through the abdomen. In one approach, an incision is made on the left side of the abdomen and the abdominal muscles are retracted to the side. Since the anterior abdominal muscle in the midline (the rectus abdominis) runs vertically, it does not need to be cut and easily retracts to the side. The abdominal contents lay inside a large sack (peritoneum) that can be retracted, thus allowing the spine surgeon access to the front of the spine without actually entering the abdomen.

After the blood vessels have been moved aside, the disc material is removed and bone graft typically with an anterior interbody cage is inserted. The ALIF approach is advantageous in that both the back muscles and nerves remain undisturbed. Another advantaged is that placing the bone graft in the front of the spine places it in compression, and bone compression tends to fuse better. Moreover, a much larger implant can be inserted through an anterior approach, providing for better initial stability of the fusion construct.

When an interbody cage is used, it is important for it to be securely anchored into vertebral bone. To this end, bone fasteners such as bone screws are used. Once implanted, the interbody cage undergoes stress and strain during normal patient activity. It is important for the interbody cage to remain securely attached to the vertebrae. While fusion will occur between the interbody cage and the vertebrae, it is important to inhibit backout of the bone fasteners.

While some interbody cages incorporate various arrangements to inhibit backout of the bone fasteners from the interbody cage after implantation, there is room for improvement.

In view of the above, it is an object of the present invention to provide an ALIF implant having an arrangement for inhibiting backout of the bone fasteners.

SUMMARY OF THE INVENTION

A spine implant for an anterior lumbar interbody fusion (ALIF) surgical procedure is provided. The spine implant is characterized by an ALIF cage, bone fasteners, and retention members that are configured to be manipulated to extend over a portion of the heads of two adjacent bone fasteners via a cam lock action to prevent backing out of the bone fasteners.

The ALIF cage is characterized by a body having an outer solid frame, particularly, but not necessarily, of a titanium alloy, a porous interior of a titanium alloy, and endplate surfaces with porous portions that are preferably, but not necessarily, made of a titanium alloy. The ALIF cage may be 3-D printed or fabricated via other methods, but in all cases the solid and porous structures are manufactured as a single piece.

The ALIF cage furthermore has a central cavity defining a bone graft area and angled bores in a front end that are configured to accept the bone fasteners such that the head of a bone fastener is retained in the angled bore, and to direct an anchoring portion of the bone fasteners up and out of the cavity. The front end also has threaded bores to receive the retention members. Lateral windows allow for visualization of the graft area on fluoroscopy images. The bone fasteners are preferably, but not necessarily, bone screws.

In one form, the bone fasteners may be curved anchoring barbs or anchoring screws.

Bone anchor retention members in the form of screws with a configured head are received in the ALIF cage in order to prevent or inhibit bone anchor back out. Rotation of the bone anchor retention members position the heads to allow a bone anchor to freely be inserted in or removed from the ALIF cage, or to prevent/inhibit a bone anchor from being removed from or received in the ALIF cage.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate the present invention, wherein.

DETAILED DESCRIPTION OF THE INVENTION

Figure 1:
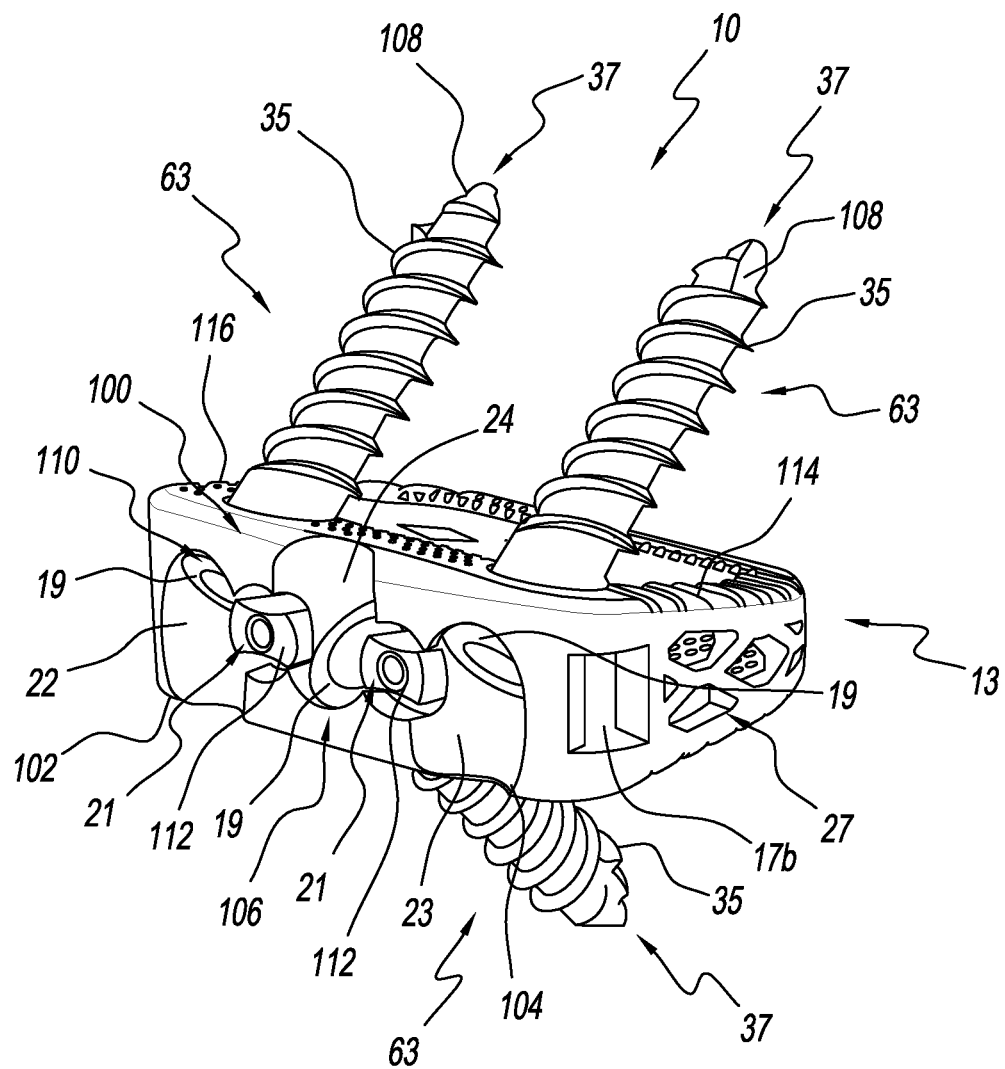
FIG. 1 is a perspective view of an ALIF implant fashioned in accordance with the present principles with bone anchoring members and retention members fully installed in an ALIF cage.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 depicts one form of an anterior lumbar interbody fusion (ALIF) implant (ALIF spine implant or ALIF implant), generally designated 10, fashioned in accordance with the present principles. The ALIF implant 10 is made from a biocompatible material that is preferably a titanium alloy, but may be PEEK, PETE, other plastic or polymer, titanium, stainless steel, an alloy of stainless steel, or otherwise. Preferably, but not necessarily, the ALIF implant 10 is manufactured as one piece that can be machined, 3-D printed or otherwise manufactured. The ALIF spine implant (spine implant) 10 includes a generally porous cage or interbody device 13 (cage) having various solid portions (or alternatively, a solid frame having various porous portions all forming a cage 13), and bone anchoring members 63 configured to retain the cage 13 to vertebrae/vertebral bone (not shown).

The ALIF implant 10 includes a retention member 21 having a head 112. When the retention member 21 is manipulated, a portion of the head 112 of the retention member 21 is configured to extend over a portion of the head 19 of an anchoring member 63 in order to inhibit, and preferably prevent, the bone anchoring member 63 from backing out. Although various configurations are contemplated herein, in the illustrated form, the ALIF implant 10 includes three (3) bone anchoring members 63 and two (2) retention members 21, with one retention member 21 situated between a first lateral bone anchoring member 63 and an adjacent medial bone anchoring member 63, and the second retention member 21 situated between a second lateral bone anchoring member 63 and the adjacent medial bone anchoring member 63. Manipulation of the one retention member 21 causes the head 112 to extend over the heads 19 of the two (2) adjacent bone anchoring members 63 (i.e. the first lateral bone anchoring member and the medial bone anchoring member) in a cam action sufficient to inhibit, and preferably prevent, the two (2) adjacent bone anchoring members 63 from backing out of the cage 13, while the manipulation of the second retention member 21 causes the head 112 to extend over the heads 19 of the two (2) adjacent bone anchoring members 63 (i.e. the second lateral bone anchoring member and the medial bone anchoring member) in a cam action sufficient to inhibit, and preferably prevent, the two (2) adjacent bone anchoring members 63 from backing out of the cage 13.

In the form described with regard to FIG. 1, the bone anchoring members 63 take the form of screw-type bone anchoring members. These screw-type bone anchoring members 63 take a generally cylindrical form and include external threading 35. A distal end 37 of the screw-type bone anchoring members 63 can include a pointed tip 108. A proximal end 110 of the bone anchoring members 63 defines a bone anchoring member head 19.

The ALIF cage 13 includes bone anchor member receiving apertures 22, 24, and 23. As illustrated, the bone anchor member receiving apertures 22, 23, and 24 extend inwardly at an angle from the front face 100 of the ALIF cage 13. As illustrated with regard to FIG. 1, the first anchor member receiving aperture 22 also being a first lateral bone anchor member receiving aperture 22 extends inwardly and upwardly from a location near the bottom left 102 of the front face 100, the second bone anchor member receiving aperture 23 also being a second lateral bone anchor member receiving aperture 23 extends inwardly and upwardly from a location near the bottom right 104 of the front face 100, and the third bone anchor member receiving aperture 24 also being a medial bone anchor member receiving aperture 24 extends inwardly and downwardly from a location near the middle 106 of the front face 100.

The bone anchor member receiving apertures 22, 23, and 24 are each configured to receive a bone anchoring member 63 therethrough, retain the head 19 thereof, and direct the distal end 37 outwardly from the cage 13 in a manner sufficient to engage into vertebrae/vertebral bone.

The proximal end 110 of the bone anchoring member 63 includes a bone anchoring member head 19. In the fully installed position depicted in FIG. 1, a portion of the head 112 of the retention member 21 is located atop a portion of the bone anchoring member heads 19 of two adjacent bone anchoring members 63 to inhibit, and preferably prevent, the movement, or backing out, of the bone anchoring members 63. This is for both retention members 21. In particular, once manipulated, a portion of the head 112 of one retention member 21 is located atop or over a portion of the first lateral bone anchoring member head 19 and a portion of the medial bone anchoring member head 19, while a portion of the head 112 of the other retention member 21 is located atop or over a portion of the second lateral bone anchoring member head 19 and a portion of the medial bone anchoring member head 19.

Figure 2:
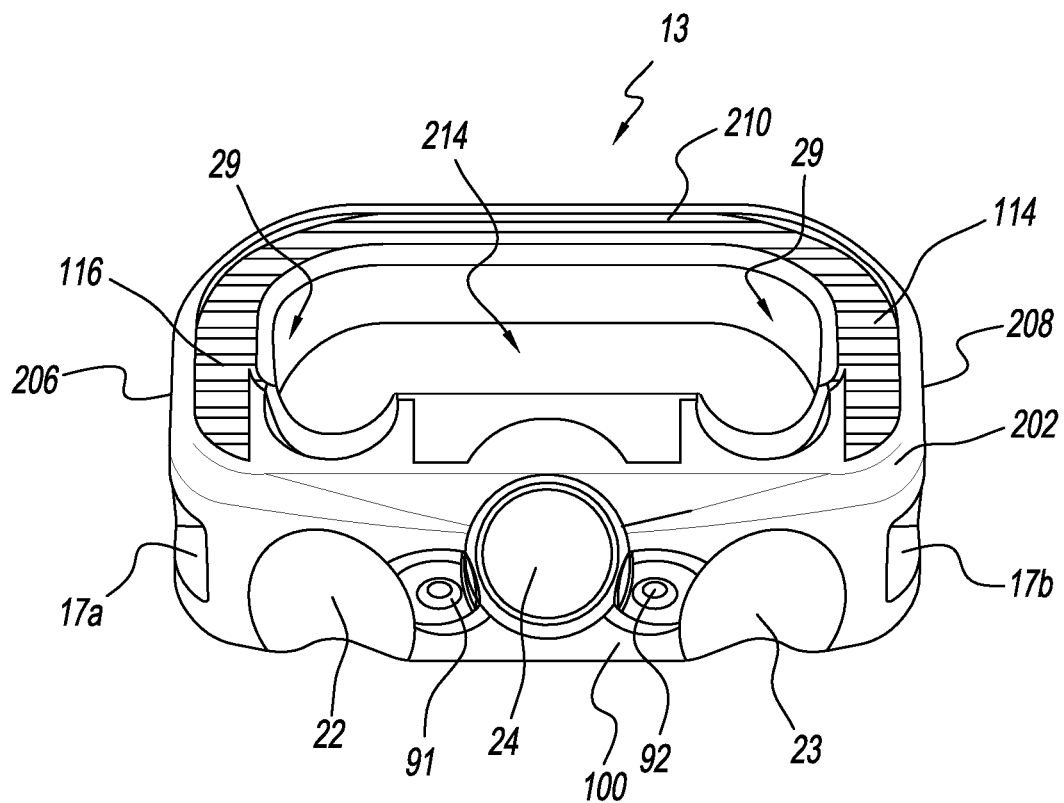
FIG. 2 is a top perspective view of the ALIF cage of FIG. 1.

The front of a bare ALIF cage 13 is particularly shown in FIG. 2. The ALIF cage 10 is characterized by a generally rectangular porous body 212 fashioned generally as a rectangular wedge having an upper (superior) surface 202, a lower (inferior) surface 204 opposite the upper surface 202, a first lateral side 206, a second lateral side 208 which is opposite to and identical with the first lateral side 206, the first end or front 100, and a second end or rear 210 opposite the front 100. As utilized herein, the nomenclature "first," "second," "front," and "rear" being arbitrary. The cage 13 includes a cavity 214 which extends from the upper surface 202 to the lower surface 204. The cavity 214 is adapted or configured to receive bone graft/bone graft material as is known to a person of ordinary skill in the art.

As is shown in FIGS. 1 and 2, the upper surface 202 of the cage 13 can include a section of serrations, teeth, or the like (collectively serrations) 114, 116. The serrations 114, 116 provide gripping of the cage 13 to a superior vertebra/vertebral bone when implanted. In a like manner, the lower surface 204 of the cage 13 can additionally include serrations (not shown) to provide gripping of an inferior vertebra/vertebral bone when implanted.

The rear 210 of the cage 13 defines a nose or arch having a downwardly angled or sloped upper (superior) surface, an upwardly angled or sloped lower (inferior) surface opposite to the downwardly angled upper surface, a first rounded side, and a second rounded side opposite to the first rounded side, the nomenclature "first" and "second" being arbitrary.

The front 100 of the cage 13 is generally planar with bone anchor member receiving apertures 22, 23, 24, at least partially directed into the cavity 214 at an angle. These bone anchor member receiving apertures 22, 23, and 24, are sized to allow the threaded shaft 35 of the bone anchoring members 63 to extend therethrough and into the cavity 214, but capture the head 19. As is illustrated in FIGS. 1 and 2, bone anchor member receiving apertures 22 and 23 are angled upwardly such that the distal end 37 of the bone anchoring members 63, which extend therethrough will extend upwardly and out of the cavity 214. Bone anchor member receiving aperture 24 is angled downwardly such that the distal end 37 of the bone anchoring member 63 which extends therethrough will extend downwardly and out of the cavity 214. In this fashion, the apertures 22, 23, and 24 direct the bone anchoring members 63 outwardly from the cavity 214 and cage 13 and into vertebrae/vertebral bone. Two sloped outlets 29 are depicted in the cage 13 which can at least partially define the exit of bone anchor receiving apertures 22 and 23. Bone anchor receiving aperture 24 additionally includes a sloped outlet. The bone anchor member receiving apertures 22, 23, 24 can be sized and angled sufficiently to permit a variable trajectory of the anchoring members 63 therethrough.

The front face 100 has a first retention member receiving portion 91 formed as a bore between bone anchor member receiving apertures 22 and 24 (the first lateral aperture 22 and the medial aperture 24). The front face 100 has a second retention member receiving portion 92 formed as a bore between bone anchor member receiving apertures 23 and 24 (the second lateral aperture 23 and the medial aperture 24). The retention member receiving portions 91 and 92 have threading to threadingly engage with the retention members 21. Rotation (manipulation) of each retention member 21 cams/positions the respective configured head 112 over portions of the heads 19 of the adjacent bone anchoring member 63 to inhibit backout of the bone anchoring members 63.

Figure 3:
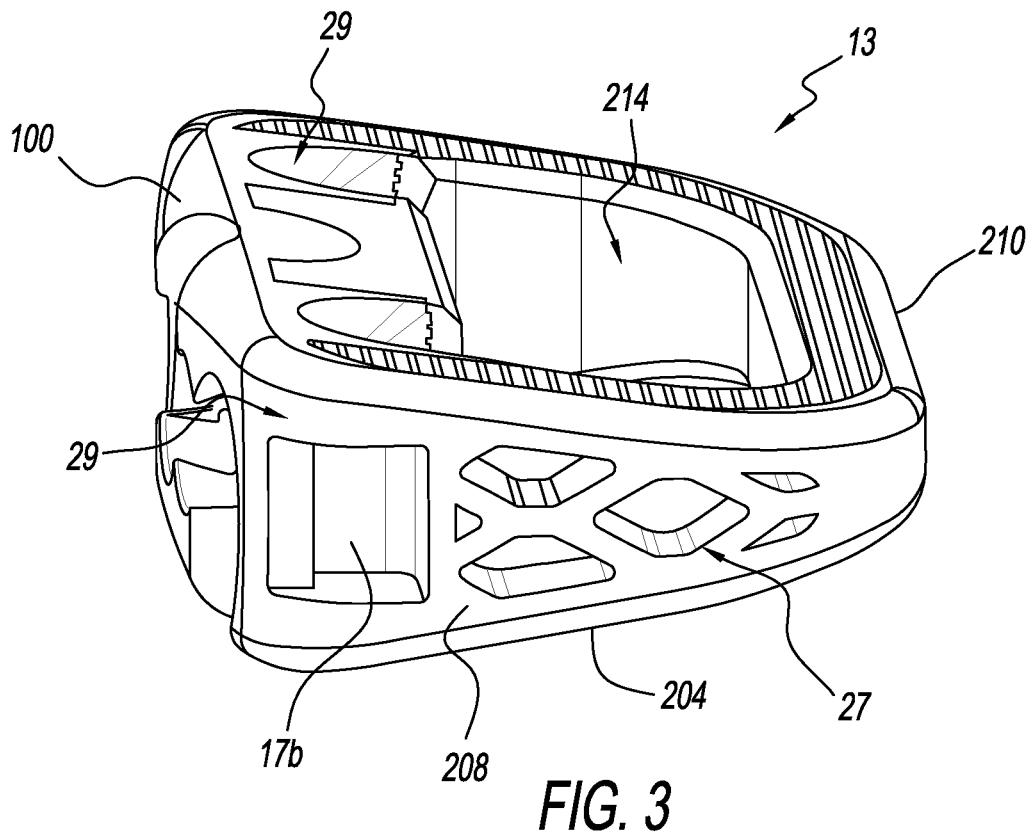
FIG. 3 is a side perspective view of the ALIF cage of FIG. 1.

Referring now to FIG. 3, a side view of the bare cage 13 is illustrated. Insertion cavities 17a, 17b, located in lateral sides 206, 208, can be utilized to provide a suitable location for an insertion tool to "grasp" the cage 13 during insertion of the ALIF implant 10. The insertion cavities 17a, 17b provide an instrument interface to enable ease of insertion of the cage 13 into the patient.

Lateral sides 206, 208, of the cage 13 can include a plurality of lateral windows 27. These lateral windows 27, depicted as having a "lattice" form, can permit for visualization of graft area (e.g. within the cavity 214) during fluoroscopy imaging.

Although the cage 13 can be constructed of a variety of biocompatible materials as was described herein, in a preferred form, the cage 13 is manufactured as a unitary structure of a titanium alloy.

Figure 4:
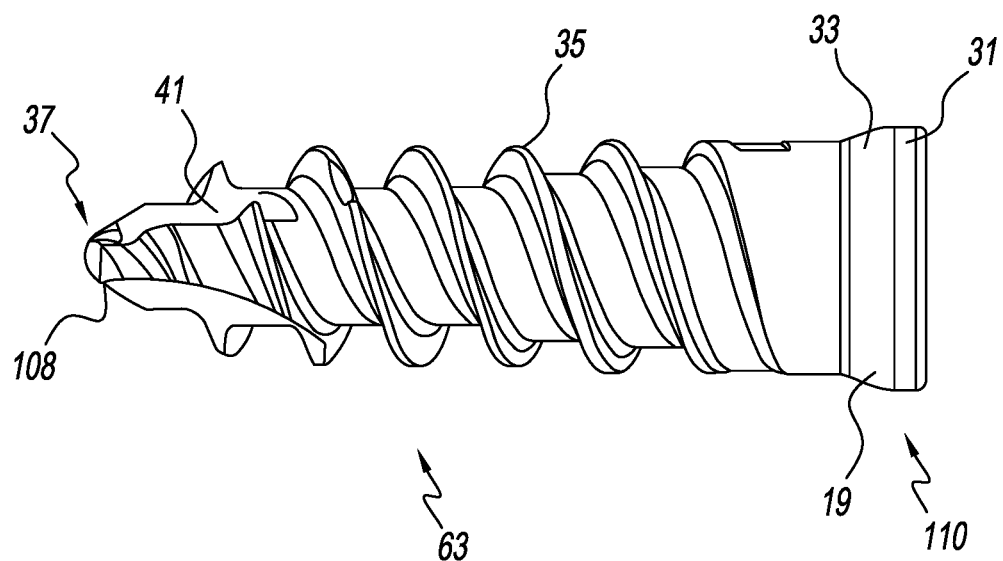
FIG. 4 is a side view of the bone anchoring member, depicted as a bone anchoring screw, of the ALIF implant of FIG. 1.

FIG. 4 displays a side view of a screw-type bone anchoring member 63. The bone anchoring member head 19 has an enlarged diameter to prevent the bone anchoring member head 19 from passing through the bone anchor member receiving aperture (e.g. 22, 23, and 24). In this manner, the distal end 37 of the bone anchoring member 63 can pass through the bone anchor member receiving aperture (e.g. 22, 23, and 24), but the bone anchoring member head 19 is retained therein. The bone anchoring member 63 can include a flat band 31 extending around a proximal end 110. The bone anchoring member head 19 is illustrated as having an angled bevel 33 configured to cooperate with an interior wall of the bone anchor member receiving aperture (e.g. 22, 23, and 24).

The threads or threading 35 permit the bone anchoring member 63 to be threaded into, and retained into a vertebrae/vertebral bone, as would be known to a person of ordinary skill in the art. The distal end 37 of the bone anchoring member 63 can include tapping portion 41 to aid the bone anchoring member during insertion into the vertebrae/vertebral bone. As would be understood, this tapping portion can aid in defining channels in the bone for the threads 35 to pass into.

Figure 5:
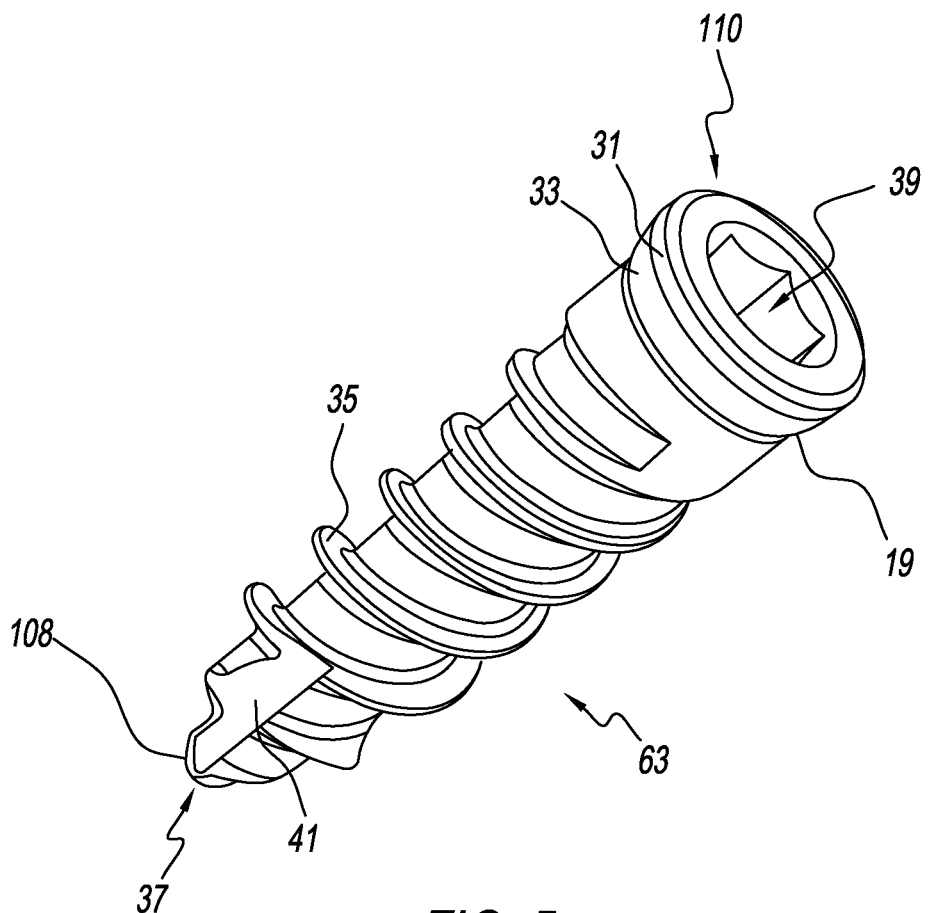
FIG. 5 is a side perspective view of the bone anchoring member of FIG. 4.
Figure 6:
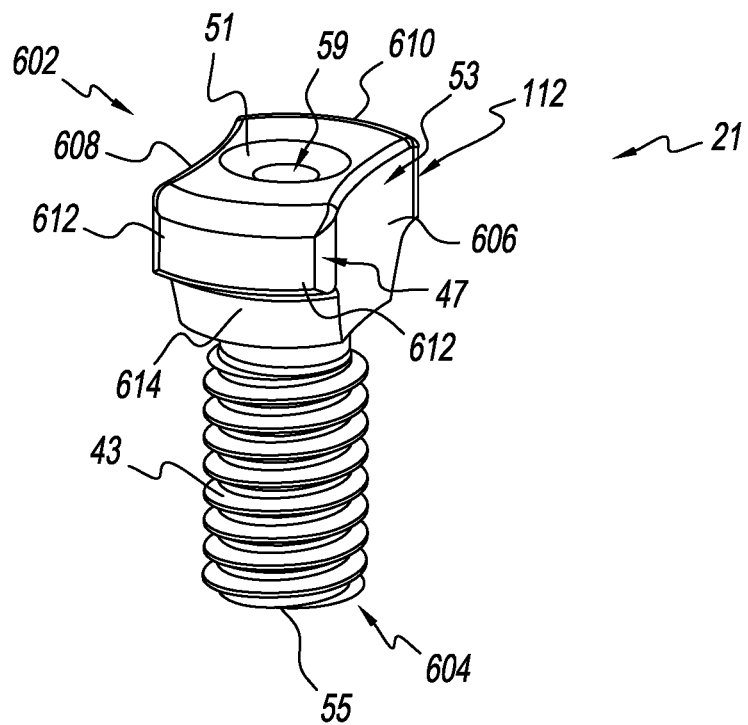
FIG. 6 depicts a perspective view of the retention member of the ALIF implant of FIG. 1.
Figure 7:
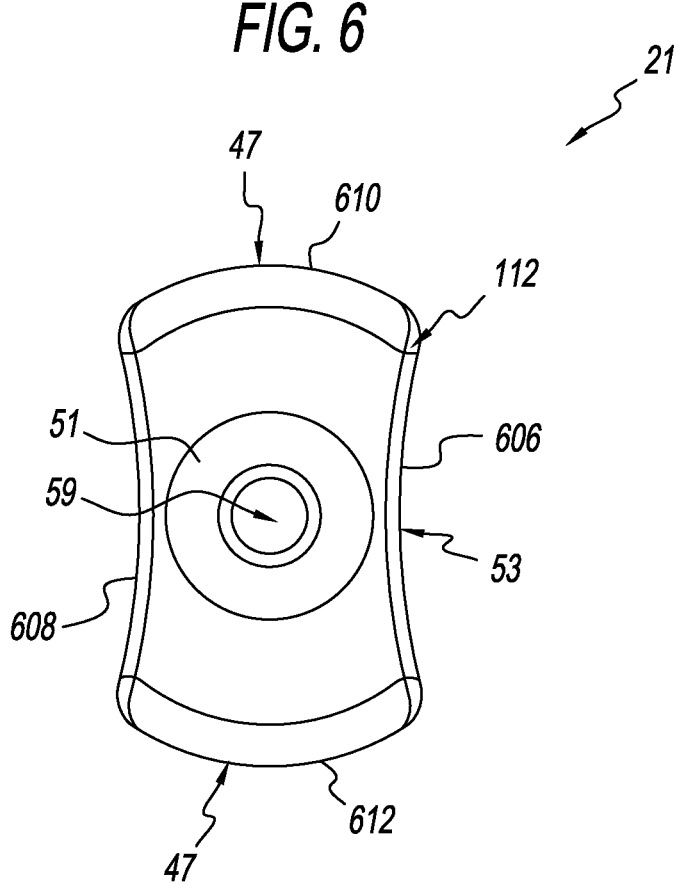
FIG. 7 is a top view of the retention member of FIG. 6.
Figure 8:
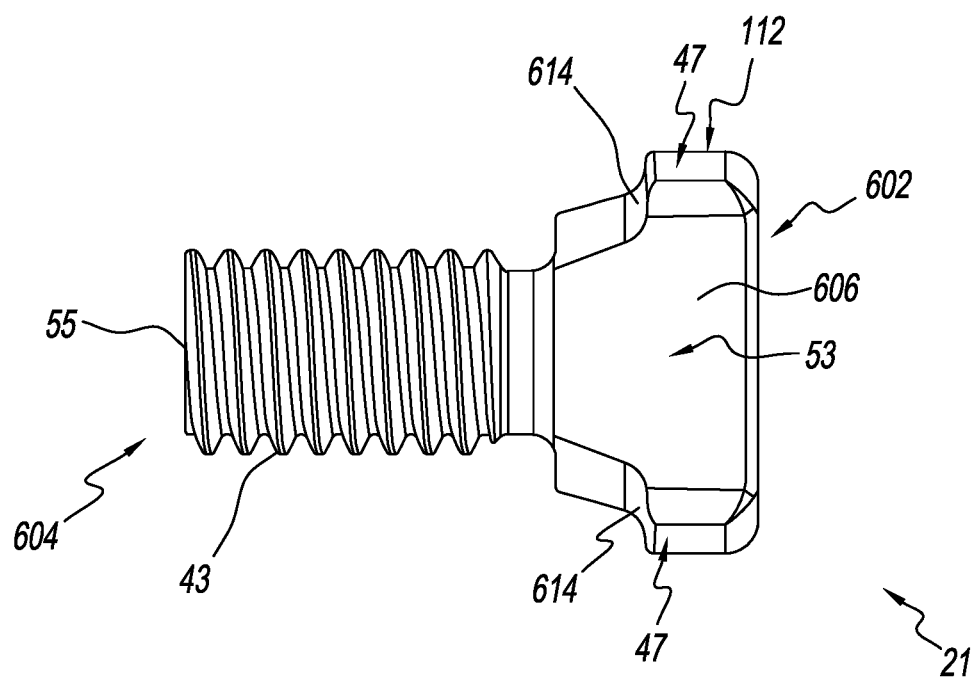
FIG. 8 is a side view of the retention member of FIG. 6.
Figure 9:
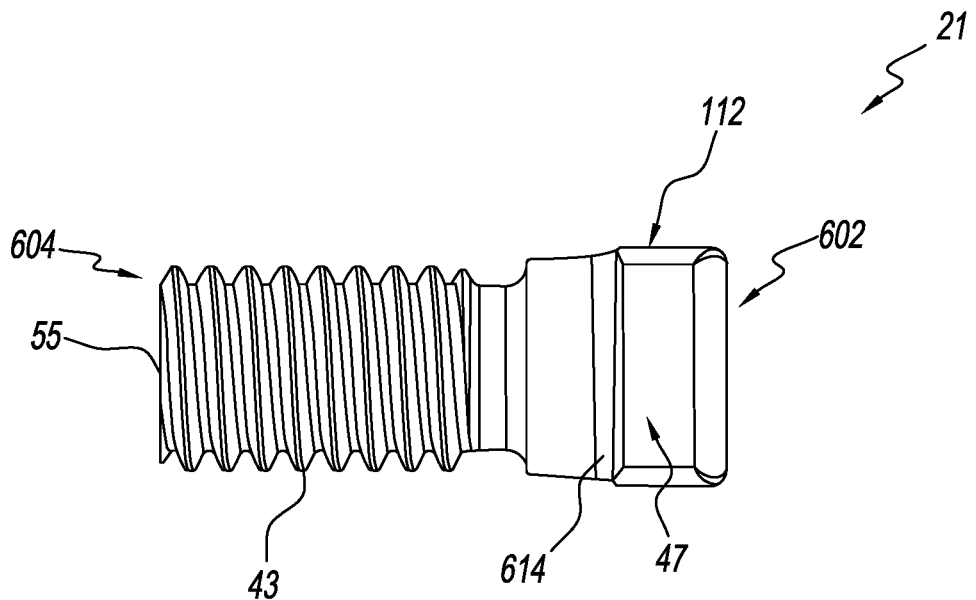
FIG. 9 is a rotated side view of the retention member of FIG. 8.

Referring now to FIG. 5, the bone anchoring member head 19 can include a tool receiving portion 39. Although tool receiving portion 39 is depicted as a hex head, a variety of tool receiving portions 39 are contemplated herein that would permit the bone anchoring member 63 to be manipulated through the cage 13 and fastened into vertebrae/vertebral bone.

FIGS. 6-9 depict the retention members 21. The retention members 21 can take the form of a cam-style bolt, as is illustrated. Each retention member 21 includes a head 112 at a proximal end 602 and threading 43 extending toward a distal end 604. The head 112 is at least partially defined by opposing outwardly arcuate sides 610, 612, and opposing inwardly arcuate sides 606, 608.

The inwardly arcuate sides 606, 608 of the retention member 21 include an inwardly tapering arc 53. This arc 53 is sized sufficiently to permit the anchoring member heads 19 to pass therethrough when the retention members 21 are rotated 90 degrees relative the configuration of FIG. 1. Specifically, in this rotated configuration, the anchoring member head 19 can be manipulated into or out of the cage 13, past the retention member head 112, absent interference from the retention member head 112. This configuration imparts the ability for the retention members 21 to be inserted into the cage 13 prior to the bone anchoring members 63. As will be discussed hereinafter, after insertion of the bone anchoring members 63, the retention members 21 can then be rotated 90 degrees such that the outwardly arcuate sides 610, 612 "cam over" the anchoring member heads 19 and prevent the bone anchoring members 63 from backing out. As would be understood by a person of skill, the size of the arc 53 can at least in part depend upon the size of the anchoring member head 19 as well as the positioning of retention members 21 relative the bone anchor member receiving apertures 22, 23, and 24.

Opposing outwardly arcuate sides 610, 612 include an outwardly protruding extension 47. A lower surface 614 of this outwardly protruding extension 47 is configured to press against the bone anchoring member head 19 in a manner sufficient to retain the bone anchoring member 63 in the cage 13. Specifically, after the bone anchoring member 63 has been inserted into the cage 13 and has been inserted into the vertebrae/vertebral bone, the retention member head 112 is rotated approximately 90 degrees. During this rotation, the lower surface 614 of the retention member head 112 comes in contact with and "cams over" the bone anchoring member head 19. The retention member head 112 is then left in this "locked" position in which the lower surface 614 exerts a force upon the bone anchoring member head 19, thereby preventing movement of the anchoring member head 19.

The head 112 of the retention member 21 can include a tool receiving portion 59. Surrounding this tool receiving portion 59 is a downwardly tapered surface 51, which can aid with insertion of the tool (not shown) into the tool receiving portion 59. It is contemplated that the tool receiving portion 59 can take a variety of forms, including, but not limited to a hex configuration, star configuration, or the like.

The retention member 21 includes threading 43 located near a distal end 604. The threading 43 is configured to mate with the threads located within retention member receiving portions 91 and 92 in a manner sufficient to permit the retention members 21 to be inserted and threadingly retained therein. In one form, a distal surface 55 of the retention member includes a substantially flat surface.

Figure 10:
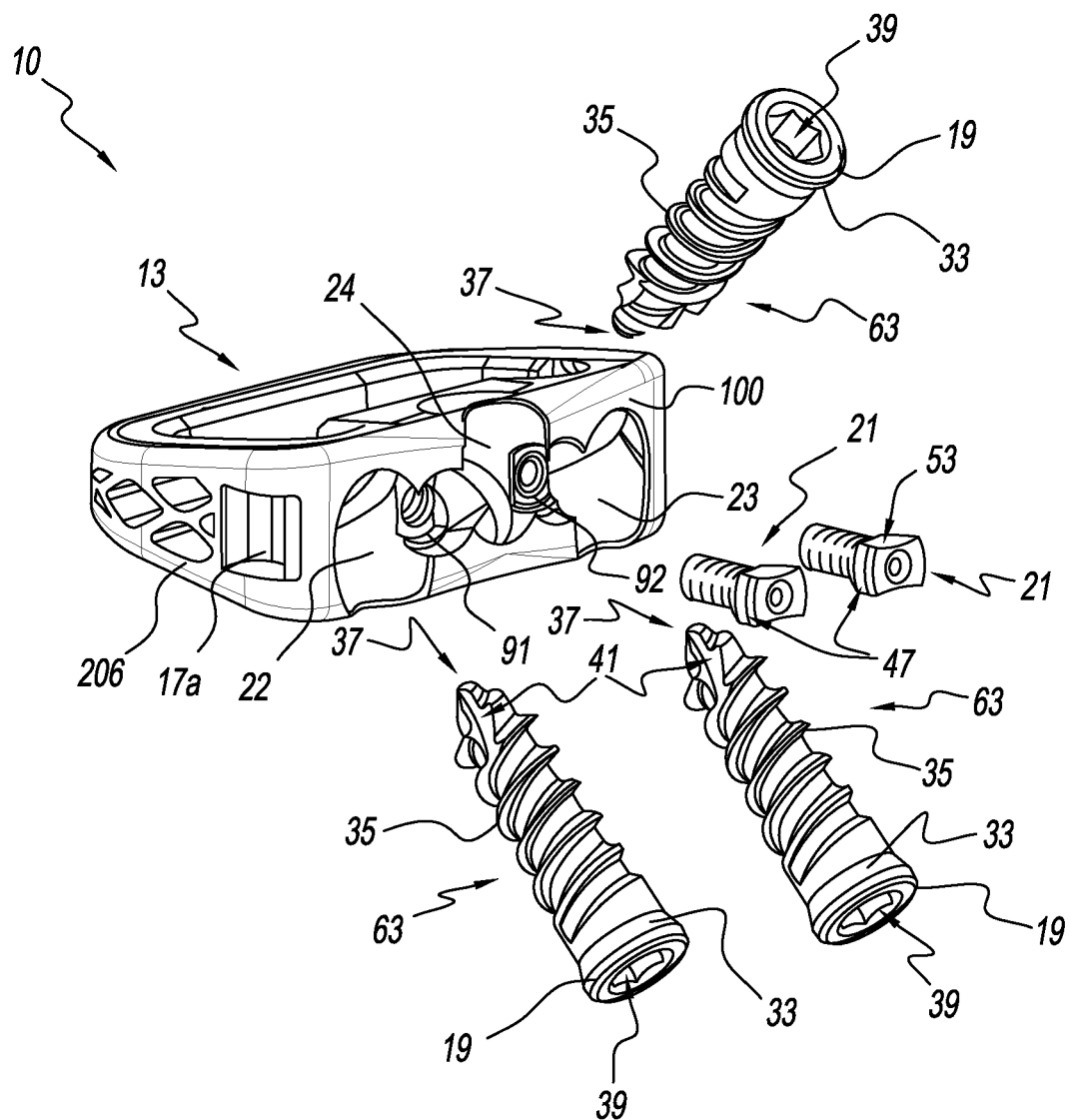
FIG. 10 is an exploded view of the ALIF implant of FIG. 1.

FIG. 10 shows an exploded view of the ALIF implant 10. This view depicts each bone anchoring member 63 at an angle which approximates the angle at which it will reside once internal to the cage 13. As was previously discussed, the retention members 21 may first be screwed into the retention member receiving portions 91 and 92. The outwardly arcuate sides 610 and 612 should be substantially parallel with the upper surface 202 and lower surface 204 of the cage (e.g. rotated 90 degrees relative the view in FIG. 10). The bone anchoring members 63 can then be inserted into the anchor member receiving apertures 22, 23, and 24, and the bone anchoring members 63 are screwed into the vertebra/vertebral bone. Once the bone anchoring members 63 are all securely inserted into the bone such that the cage 13 is retained to the bone, the retention members 21 are rotated 90 degrees such that at least a portion of the protruding extensions 47 rest atop at least a portion of the bone anchoring member heads 19 and inhibit the backing out of the bone anchoring member heads 19.

Figure 11:
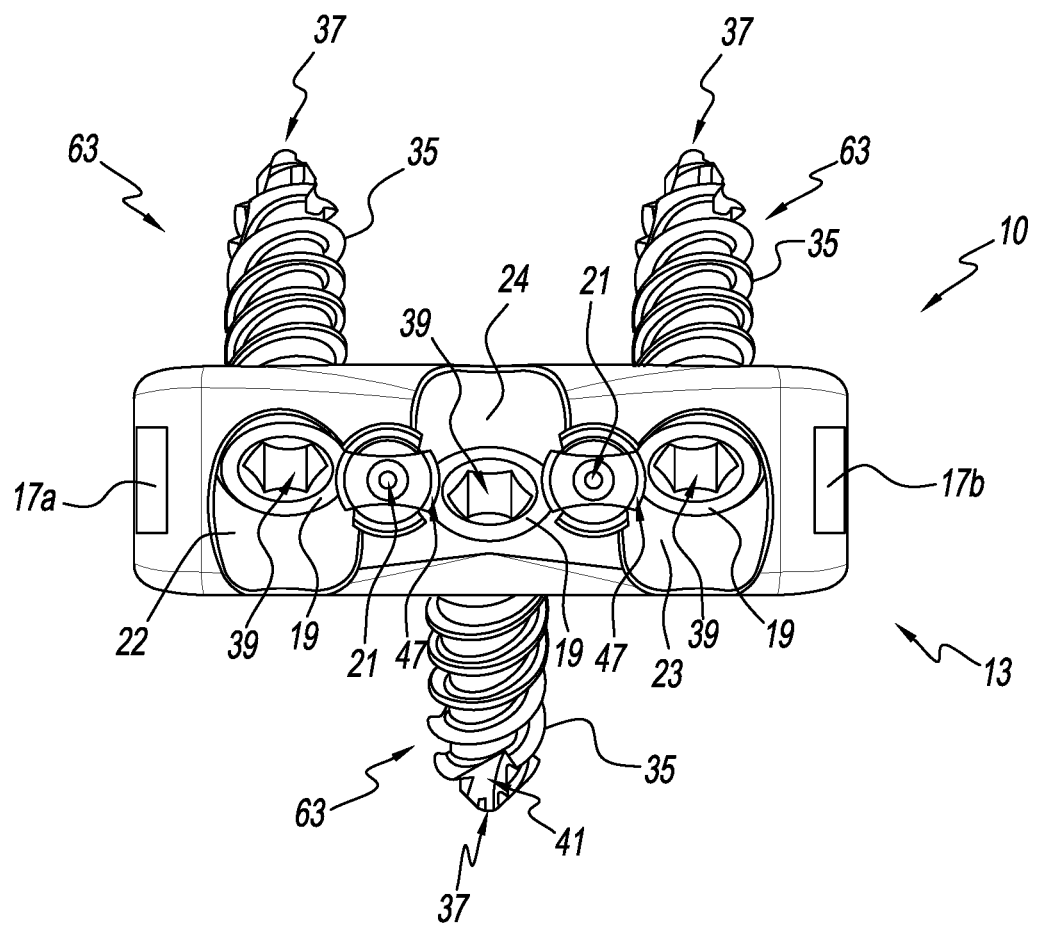
FIG. 11 depicts a front view of the ALIF implant of FIG. 1, having the bone anchoring members and retention members fully installed therein.
Figure 12:
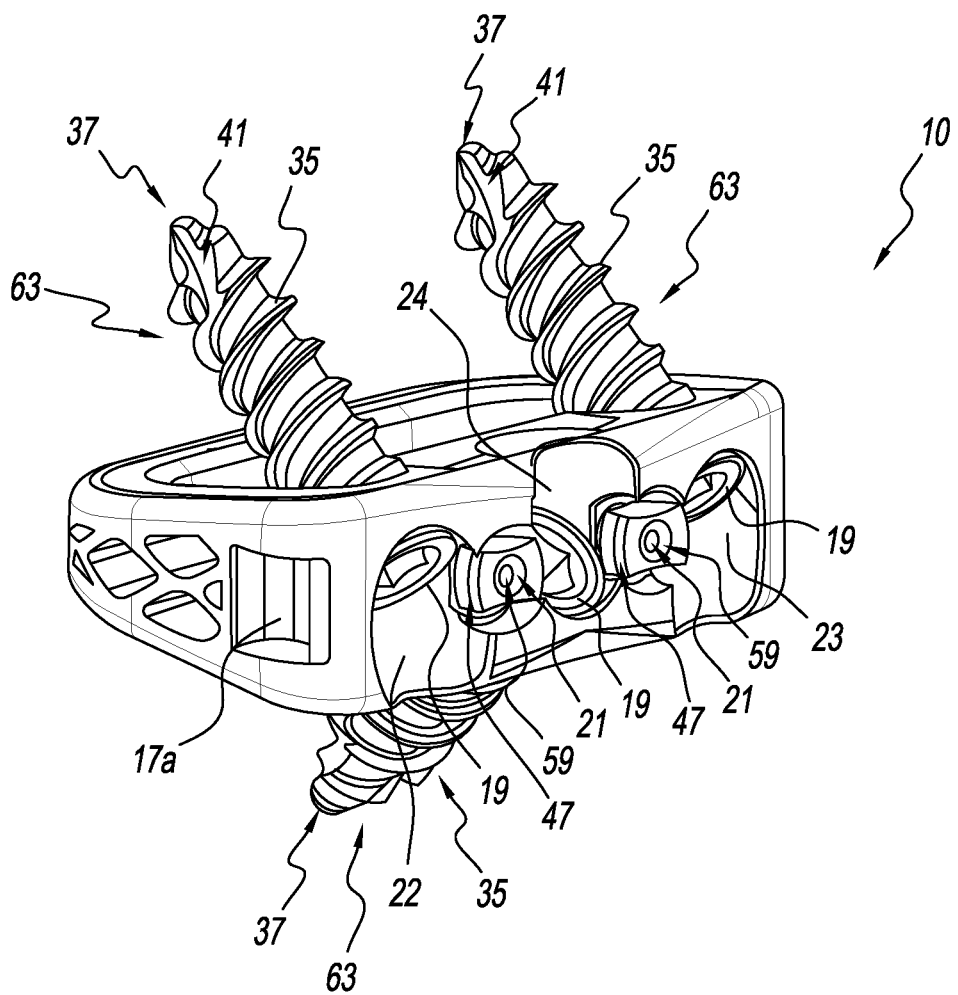
FIG. 12 is a further perspective view of the ALIF implant of FIG. 11.
Figure 13:
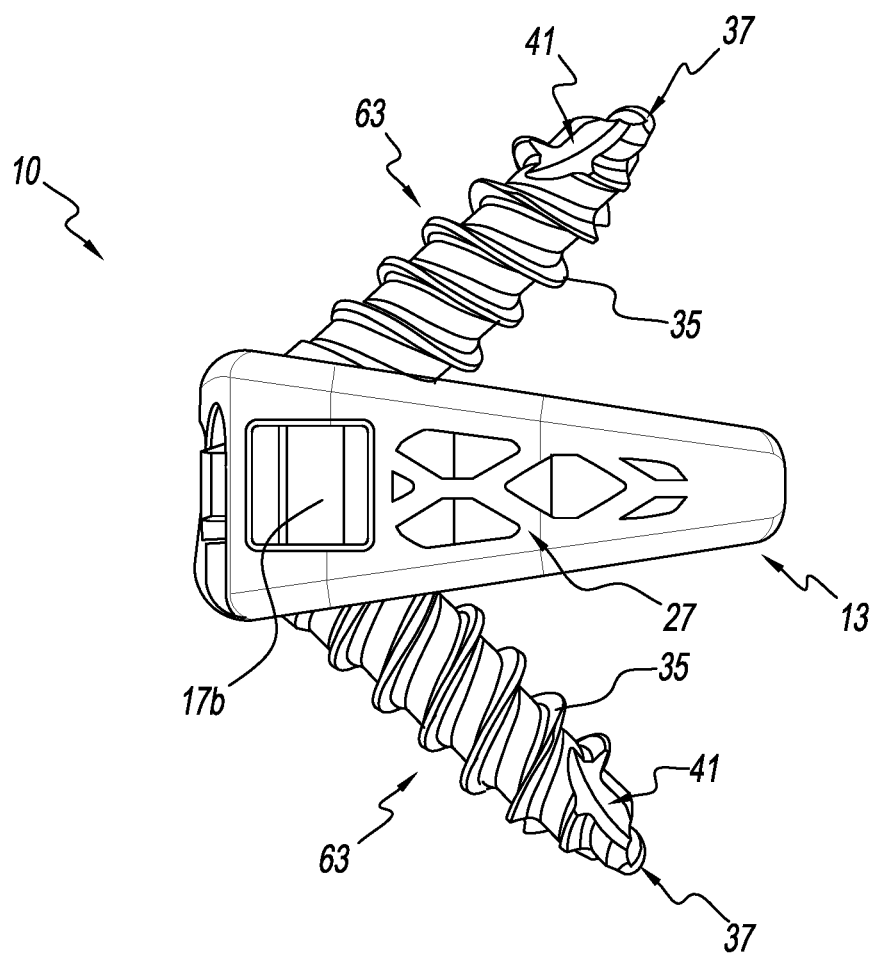
FIG. 13 is a side view of the ALIF implant of FIG. 11.

FIG. 11 depicts a front view of the ALIF implant 10 depicting the fully inserted anchoring members 63 and fully inserted retention members 21 resting atop the anchoring member heads 19. As was discussed, in this fully inserted position, the protruding extensions 47 of the retention members 21 prevent the anchoring members 63 from withdrawing from the cage 13. FIG. 12 depicts a perspective view of the fully assembled ALIF implant 10 of FIG. 11. FIG. 13 presents a side view of the fully assembled ALIF implant 10 of FIG. 11, illustrating the lateral windows 27 and the outward angles of anchoring members 63.

Figure 14:
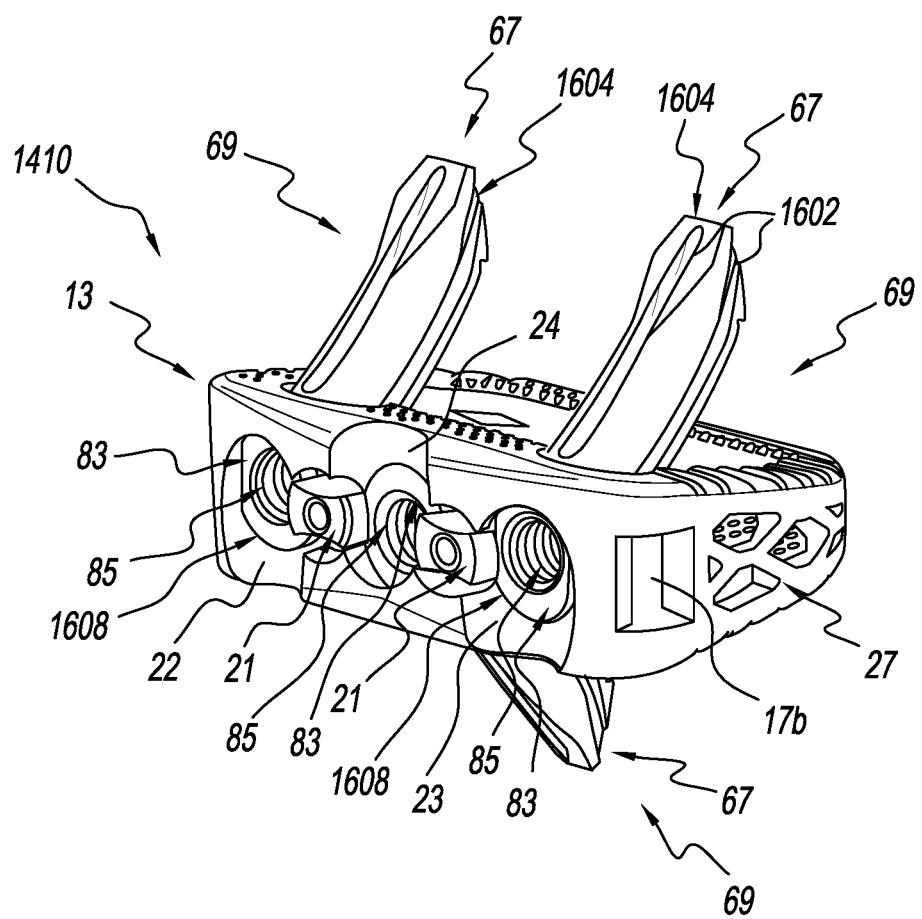
FIG. 14 depicts a further form of an ALIF implant fashioned in accordance with the present principles.
Figure 15:
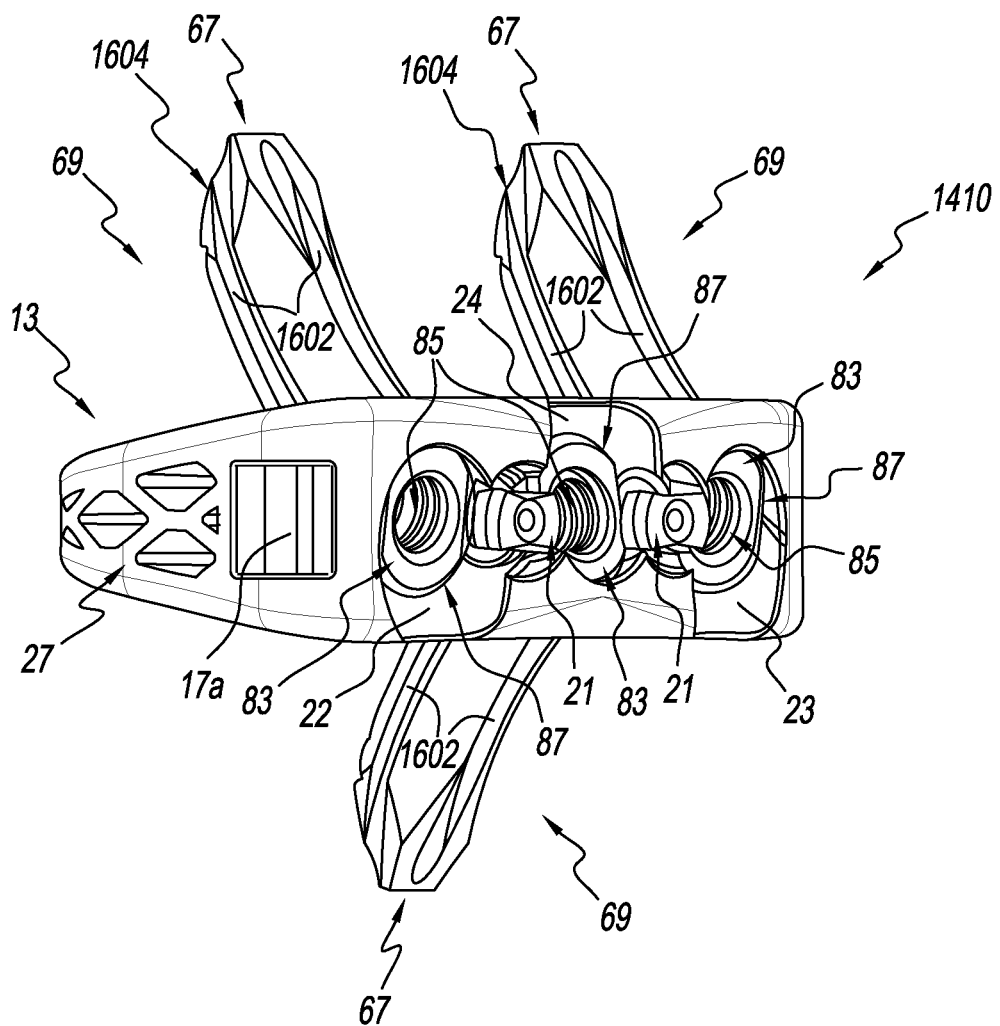
FIG. 15 is a perspective view of the ALIF implant of FIG. 14.
Figure 16:
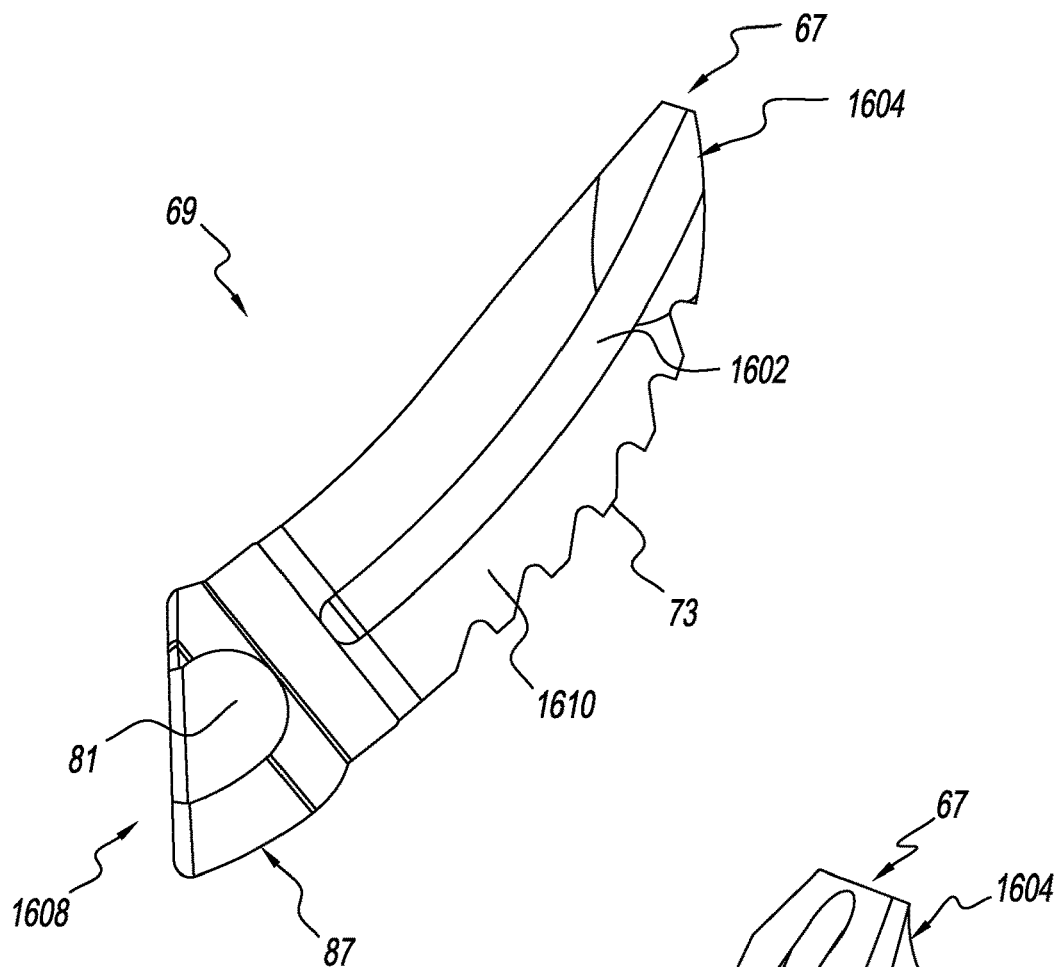
FIG. 16 depicts a side view of a bone anchoring barb of the ALIF implant of FIG. 14.
Figure 17:
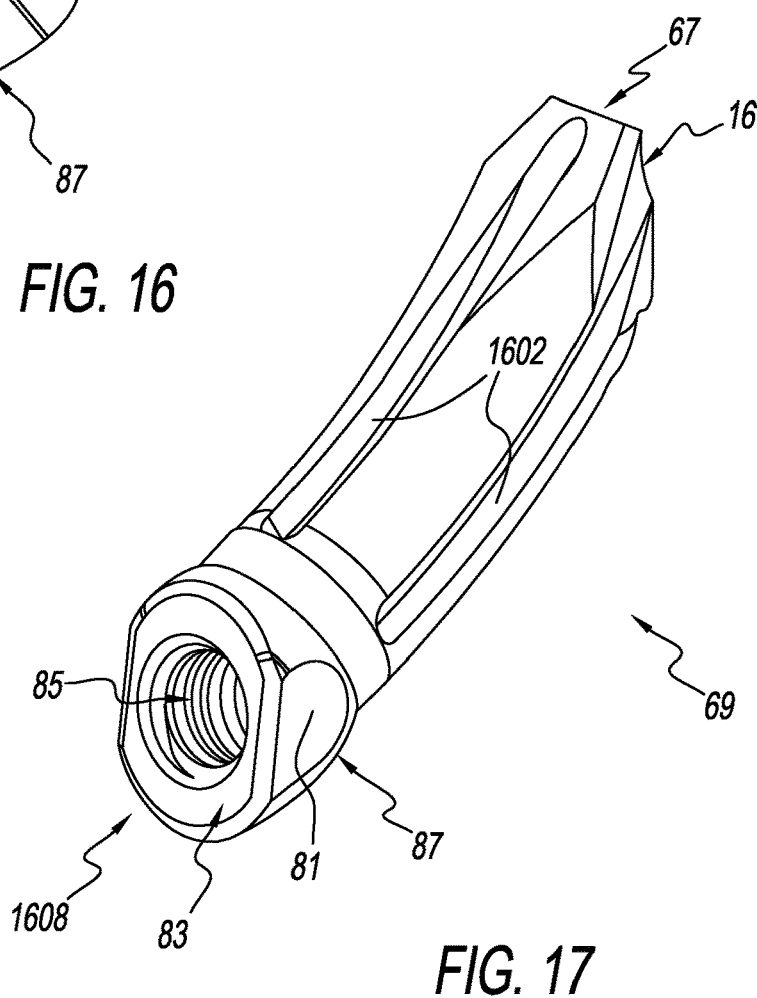
FIG. 17 is a perspective view of the bone anchoring barb of FIG. 16.

FIGS. 14-16 depict an alternate form of an ALIF implant. The primary difference between ALIF implant 1410 and ALIF implant 10 is the use of bone anchoring barbs 69 in implant 1410 rather than screw-type bone anchoring members 63 as were utilized in implant 10. Referring now to FIGS. 16-17, one form of a bone anchoring barb 69 will now be described. The bone anchoring barb 69 includes a curvature extending between a proximal end 1608 and a distal end 67. A plurality of serrations or teeth 73 are located on an outwardly arcuate surface 1610 of the bone anchoring barb 69. The bone anchoring barb 69 includes a plurality of grooves or channels 1602. As illustrated, the bone anchoring barb 69 includes one groove 1602 per side. The serrations 73 and grooves 1602 permit the bone anchoring barb 69 to fixedly anchor against a vertebrae/vertebral bone. A distal end 67 of the bone anchoring barb 69 can include a beveled tip 1604 which is structured for insertion into the vertebrae/vertebral bone.

The bone anchoring barb 69 includes a head 87. The head 87 includes a front surface 83 which takes a substantially circular shape with opposing flattened portions 81. To insert the bone anchoring barb 69, a tool (not shown) is inserted into a threaded tool retention portion 85. The bone anchoring barb 69 can then be inserted into an anchor member receiving aperture 22, 23, and/or 24 of the cage 13 and is fixedly inserted into the vertebrae/vertebral bone. As was discussed with regard to ALIF implant 10, after the bone anchoring barbs 69 have been properly engaged with the vertebrae/vertebral bone, the retention members 21 are "cammed" over the front surface 83. The outwardly arcuate sides 610 and 612 of the retention member 21 can additionally act upon and engage with the flattened portions 81 of the head 87. The force exerted by the retention members 21 onto the flattened portions 81 and front surface 82 is sufficient to prevent withdraw (e.g. backing out) of the bone anchoring barbs 69 from the bone and/or cage 13. The retention members 21 can additionally provide a force against the bone anchoring barbs 69 to ensure the bone anchoring barbs 69 remain fixedly connected to the vertebrae/vertebral bone.

Referring back to FIG. 15, a further view of an assembled ALIF implant 1410 is depicted with bone anchoring barbs 69 and retention members 21 fully inserted into the cage 13.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A spine implant for an ALIF procedure, the spine implant comprising:

a plurality of anchoring members each having a shaft, a head on one end of the shaft, and a tip on another end of the shaft;

a porous cage having a front, a rear, a central cavity, an upper surface, a lower surface, a first angled bore in a first lateral side of the front that extends into the central cavity, a second angled bore in a second lateral side of the front that extends into the central cavity, and a third angled bore in the front between the first angled bore and the second angled bore that extends into the central cavity, the first angled bore extending from proximate the upper surface to through the lower surface, the second angled bore extending from proximate the upper surface to through the lower surface, and the third angled bore extending from the lower surface to through the upper surface, wherein each of the first, second, and third angled bores is configured to receive one of the plurality of anchoring members therethrough in a manner such that the tips of the anchoring members are directed out of the cavity; and two retention members each having a retention member head and configured for insertion into the front in a manner such that at least a portion of the retention member heads of each retention member is located over the head of adjacent anchoring members, and wherein the retention member head of each retention member is further configured to inhibit backout of the adjacent anchoring members in the porous cage via cam action onto the heads of the adjacent anchoring members.

2. The spine implant of claim 1, wherein the retention members further include a retention member shaft, and wherein an underside portion of each retention member head rests upon the heads of the adjacent anchoring members.

3. The spine implant of claim 2, wherein each retention member head further includes two opposing sides that are greater in length than remaining sides of the retention member head.

4. The spine implant of claim 2, wherein the front further includes a first threaded retention member receiving portion located between the first angled bore and the third angled bore, wherein the threaded retention member receiving portion is configured to receive and retain a threaded distal end of the retention member therein.

5. The spine implant of claim 4, further comprising a second threaded retention member receiving portion located between the second angled bore and the third angled bore, and wherein the second threaded retention member receiving portion is configured to receive and retain a second retention member therein.

6. The spine implant of claim 1, wherein the porous cage has a first lateral side and a second lateral side that are both unitary with the front and the rear of the porous cage.

7. The spine implant of claim 6, wherein the first and the second lateral sides contain windows.

8. The spine implant of claim 1, wherein the plurality of anchoring members further comprise barb-type anchoring members.

9. The spine implant of claim 1, wherein the porous cage consists of titanium alloy.

10. The spine implant of claim 1, wherein the head of each anchoring member is located near the front of the porous cage and the tip of each anchoring member is located closer toward the rear of the porous cage, being angled away from the porous cage.

* * * * *